United States Patent [19]
Keenan et al.

[11] Patent Number: 5,401,891
[45] Date of Patent: Mar. 28, 1995

[54] PRODUCTION OF POLYMERIZATION GRADE DICYCLOPENTADIENE

[75] Inventors: Michael J. Keenan; David W. Sharp; Robert C. Schucker, all of Baton Rouge, La.

[73] Assignee: Exxon Chemical Patents Inc., Linden, N.J.

[21] Appl. No.: 169,847

[22] Filed: Dec. 17, 1993

[51] Int. Cl.$^6$ ............... C07C 7/00; C07C 7/144; C07C 1/00

[52] U.S. Cl. ............... 585/318; 585/818; 585/803

[58] Field of Search ............... 585/803, 818, 318

[56] References Cited

U.S. PATENT DOCUMENTS

| | | | |
|---|---|---|---|
| 3,745,744 | 7/1973 | Perry et al. | 55/16 |
| 3,773,844 | 11/1973 | Perry et al. | 260/669 A |
| 4,914,064 | 4/1990 | Schucker | 502/4 |
| 4,944,880 | 7/1990 | Ho et al. | 210/640 |
| 4,990,275 | 2/1991 | Ho et al. | 252/62.3 |
| 5,063,186 | 11/1991 | Schucker | 502/4 |

Primary Examiner—Helen M. S. Sneed
Assistant Examiner—Nhat D. Phan
Attorney, Agent, or Firm—J. J. Mahon

[57] ABSTRACT

A process for purifying crude dicyclopentadiene which comprises the steps of: cracking the crude dicyclopentadiene to form a monomeric-containing effluent which comprises at least one monomer selected from the group consisting of: $C_4$ acyclic dienes, $C_5$ acyclic dienes, cyclopentadiene and methylcyclopentadiene; separating the monomeric-containing effluent into a cyclopentadiene-enriched stream and a cyclopentadiene-poor stream; dimerizing the cyclopentadiene-enriched stream to form a dimerizer effluent; contacting a membrane separator under pervaporation conditions with the dimerizer effluent wherein the $C_4$ acyclic dienes, $C_5$ acyclic dienes and cyclopentadiene permeate through the membrane separator and wherein a dicyclopentadiene product having a purity of at least about 98% is retained as retentate.

17 Claims, 2 Drawing Sheets

PRODUCTION OF POLYMERIZATION GRADE DICYCLOPENTADIENE

The present invention relates generally to the purification of dicyclopentadiene to a quality suitable for metathesis polymerization. This unique purification method comprises selective cracking of low purity dicyclopentadiene to monomeric cyclopentadiene, distillation, selective dimerization, and final purification via membrane pervaporation.

BACKGROUND OF THE INVENTION

Dicyclopentadiene (DCPD) is an item of commerce and is produced in the steamcracking of gas oils, naphthas, and other hydrocarbons. It is usually obtained as a by-product from the steamcracker effluent after distillation and heat-soaking of the effluent. Unfortunately, the crude DCPD produced by steam cracking is typically of low purity which is unacceptable for metathesis polymerization.

Various methods have been used to purify the crude DCPD. One such purification method involves the distillation of crude DCPD to remove low boiling compounds such as butadiene, isoprene, pentadienes, and cyclopentadiene (CPD). This is followed by a second stage distillation or is done as a side stream operation to provide a higher purity DCPD.

This distillation method has the disadvantage of low recovery of DCPD of suitable quality for metathesis polymerization. Yields are typically 70% or less. Additionally, it has the disadvantage of being susceptible to oxygen leaks. These leaks give rise to the formation of oxygenated compounds which inhibit metathesis polymerization.

Another method of DCPD purification is to thermally crack DCPD and some of the codimers of cyclopentadiene (CPD) and $C_4$ and $C_5$ acyclic dienes in (1) a kettle-type reboiler (e.g., a shell and tube heat exchanger); (2) a vapor phase cracker; and (3) a thermosyphon reboiler with an inert hydrocarbon diluent to reduce fouling. The monomers which are the effluent of these systems can then be separated via conventional distillation to provide a monomer concentrate highly enriched in CPD. Controlled dimerization of this CPD stream can afford DCPD in concentrations of greater than 98%.

This thermal cracking/dimerization method does not give directly a DCPD of purity suitable for metathesis polymerization. The DCPD must be fractionally distilled to remove the aforementioned low-boiling $C_4$ and $C_5$ acyclic dienes and CPD. Long dimerizer residence times at elevated temperatures (i.e., greater than 83° C.) can give rise to the formation of codimers of CPD and $C_4$ and $C_5$ acyclic dienes. Some of these codimers, such as tetrahydroindene and 6-methyltetrahydroindene, are known to inhibit metathesis polymerization. Additionally, the dimerization conditions and/or distillation conditions can give rise to the formation of CPD trimers. These trimers may polymerize at rates different from DCPD and may alter the structural properties of the poly(DCPD).

The present inventors have developed a unique process which overcomes the low purity problems associated with conventional distillation methods and the formation of codimers which results from the conventional thermal cracking/dimerization methods discussed above. In either case, the resultant dimerization product inhibits metathesis polymerization which is a highly desirable commercial application for dicyclopentadiene.

The present invention also provides many additional advantages which shall become apparent as described below.

SUMMARY OF THE INVENTION

A process for purifying crude dicyclopentadiene which comprises the steps of: cracking the crude dicyclopentadiene to form a monomeric-containing effluent which comprises at least one monomer selected from the group consisting of: $C_4$ acyclic dienes, $C_5$ acyclic dienes, cyclopentadiene and methylcyclopentadiene; separating the monomeric-containing effluent into a cyclopentadiene-enriched stream and a cyclopentadiene-poor stream; dimerizing the cyclopentadiene-enriched stream to form a dimerizer effluent; contacting a membrane separator under pervaporation conditions with the dimerizer effluent wherein the $C_4$ acyclic dienes, $C_5$ acyclic dienes and cyclopentadiene permeate through the membrane and wherein a dicyclopentadiene product having a purity of at least 98% does not permeate through the membrane and, thus, is retained as retentate.

The process of the present invention may preferably include an additional step of condensing the cyclopentadiene-enriched stream. Furthermore, the present invention may also comprise a step of recovering the monomeric-containing effluent produced during the cracking step.

Additionally, the present invention comprises a system for purifying crude dicyclopentadiene which comprises: a means for cracking the crude dicyclopentadiene to form a monomeric-containing effluent which comprises at least one monomer selected from the group consisting of: $C_4$ acyclic dienes, $C_5$ acyclic dienes, cyclopentadiene and methylcyclopentadiene; a means for separating the monomeric-containing effluent into a cyclopentadiene-enriched stream and a cyclopentadiene-poor stream; a means for dimerizing the cyclopentadiene-enriched stream to form a dimerizer effluent; at least one membrane which is capable of passing therethrough $C_4$ acyclic dienes, $C_5$ acyclic dienes and cyclopentadiene, as permeate, and retaining a dicyclopentadiene product having a purity of at least 98%, as retentate.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
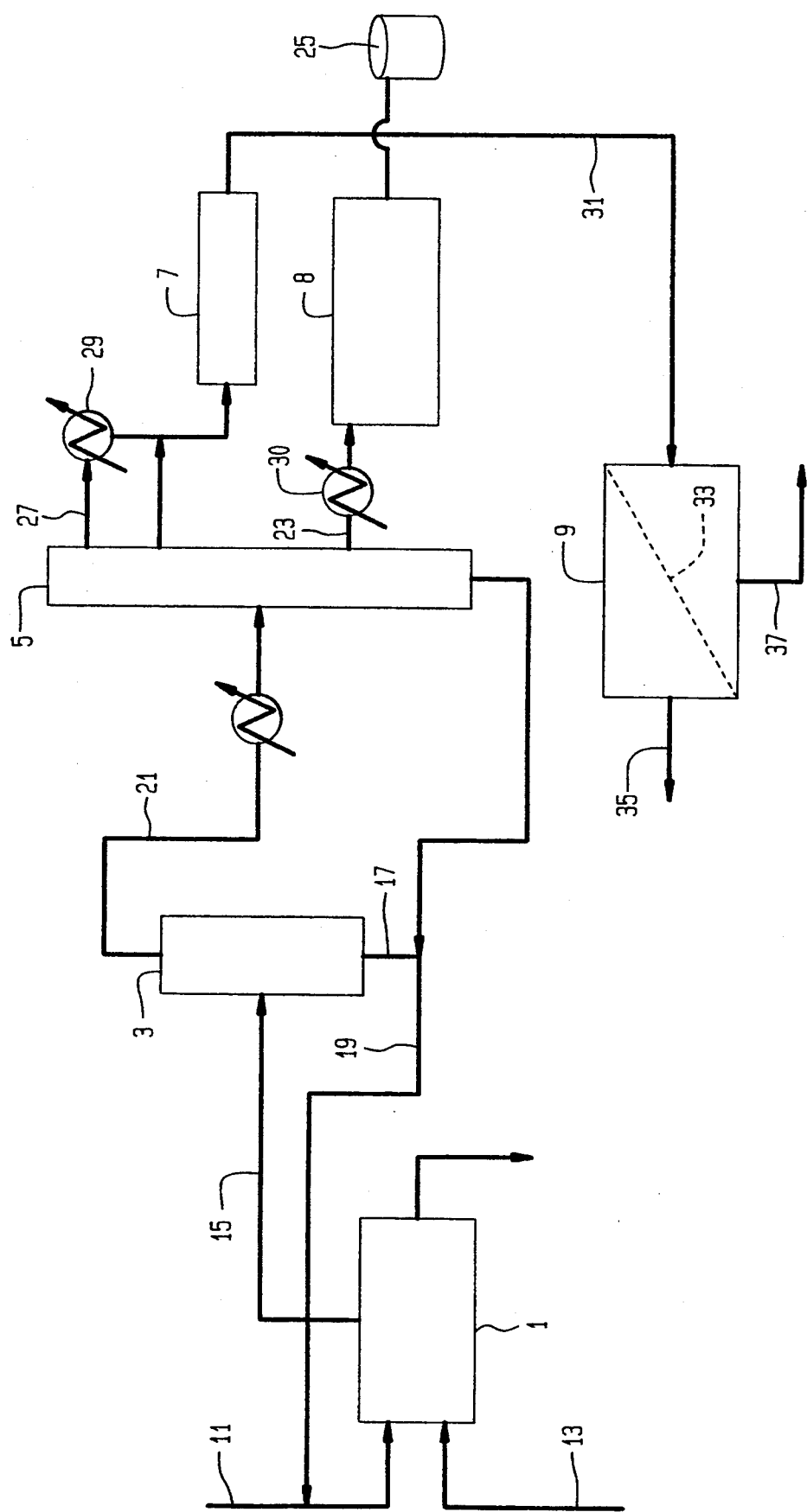
FIG. 1 is a block flow diagram of the dicyclopentadiene purification system in accordance with the present invention.

The present invention broadly pertains to a process for obtaining polymerization grade dicyclopentadiene (DCPD) via membrane purification. This process comprises the following primary steps: (a) cracking of crude DCPD to form a monomeric-containing effluent (C4 and C5 acyclic dienes, cyclopentadiene (CPD) and methylcyclopentadiene (MCPD)) in a shell and tube heat exchanger; (b) recovery and distillation of the monomers from the monomeric-containing effluent of the heat exchanger to provide a CPD-enriched stream and a CPD poor stream; (c) condensing and dimerizing the CPD-enriched stream under conditions such that 60 to 85% of the CPD is dimerized; and (d) separation of the dimerizer effluent such that C4 and C5 acyclic dienes and CPD permeate through a membrane under pervaporation conditions wherein a high purity (i.e., 98–99%) DCPD product is retained as retentate.

Pervaporation is a membrane process used to separate mixtures of dissolved solvents. In typical pervaporation processes, a liquid mixture contacts one side of a membrane such that the permeate is removed as a vapor from the other side. Transport through the membrane is induced by the difference in partial pressure between the liquid feed solution and the permeate vapor. This partial-pressure difference can be maintained in several ways. In the laboratory a vacuum pump is usually used to draw a vacuum on the permeate side of the system. Industrially, the permeate vacuum is most economically generated by cooling the permeate vapor, causing it to condense. The components of the feed solution permeate the membrane at rates determined by their feed solution vapor pressures, that is, their relative volatilities and their intrinsic permeabilities through the membrane. Pervaporation has elements in common with air and steam stripping, in that the more volatile contaminants are usually, although not necessarily, preferentially concentrated in the permeate. However, during pervaporation no air is entrained with the permeating organic, and the permeate solution is many times more concentrated than the feed solution, so that its subsequent treatment is straightforward.

The separation factor, $\beta_{pervap}$, achieved by a pervaporation process can be defined in the conventional way as follows:

$$\beta_{pervap} = \frac{(c''_i/c''_j)}{(c'_i/c'_j)}$$

where $c'_i$ and $c'_j$ are the contractions of components (i) and (j) on the feed liquid side and $c''_i$ and $c''_j$ are the concentrations of components (i) and (j) on the permeate side of the membrane. Because the permeate is a vapor, $c''_i$ and $c''_j$ can be replaced by $p''_i$ and $p''_j$, the vapor pressures of components (i) and (j) on the permeate side of the membrane. The separation achieved can then be expressed by the following equation:

$$\beta_{pervap} = \frac{(p''_i/p''_j)}{(c'_i/c'_j)}$$

Particularly desirable pervaporation membranes for use in the present invention may be selected from the group consisting of: any rubbery membrane (i.e., membranes whose glass transition temperature is below the operating temperature), polyester imide membranes, and polyurea/urethane membranes.

One preferred rubbery membrane is a silicone rubber membrane such as polydimethylsiloxane.

The polyester imide membranes are preferably those membranes formed from a copolymer composition with a hard segment of a polyimide and a soft segment of an oligomeric aliphatic polyester, wherein the hard and soft segments are alternating, the polyimide is derived from a dianhydride and a diamine, and the oligomeric aliphatic polyester is a polyadipate, a polysuccinate, a polymalonate, a polyoxalate or a polyglutarate. Suitable polyester imide membranes are disclosed in U.S. Pat. Nos. 4,944,880 (Ho et al.), which issued on Jul. 31, 1990, and 4,990,275 (Ho et al.), which issued on Feb. 5, 1991, both of which are incorporated herein by reference.

The polyurea/urethane membranes are preferably symmetric, dense film membranes made from the corresponding polyurea/urethane copolymers by standard membrane casting techniques. The polyurea/urethane copolymers are produced by reacting dihydroxy or polyhydroxy compounds, such as polyesters or polyesters having molecular weights in the range of about 500 to about 5000 with aliphatic, alkylaromatic or aromatic diisocyanates or polyisocyanates and low molecular weight chain extenders, such as diamines, polyamines or amino alcohols.

Various polyurea/urethane membranes are disclosed in U.S. Pat. Nos. 4,914,064 (Schucker), which issued on Apr. 3, 1990, and 5,063,186 (Schucker), which issued on Nov. 5, 1991, both of which are incorporated herein by reference.

The present invention can best be described by reference to the attached drawings, wherein FIG. 1 is a schematic representation of the preferred DCPD membrane purification system. This purification system is extremely useful in producing metathesis polymerization grade DCPD and comprises a shell and tube heat exchanger 1, a phase separator 3, distillation tower 5, dimerizer reactor 7, and membrane separator 9.

This system can be used to purify DCPD to approximately 98–99% in accordance with the following steps.

Initially, low purity DCPD is delivered via conduit 11 to shell and tube heat exchanger 1 wherein it is cracked to monomers (i.e., C4 and C5 acyclic dienes, cyclopentadiene (CPD), and methylcyclopentadiene (MCPD)). Heat exchanger 1 is operated with the shell side as the process side. An inert hydrocarbon heat transfer oil having a boiling point greater than the crude DCPD is delivered via conduit 13 to heat exchanger 1. The heat transfer oil is added to increase cracking efficiency and to reduce exchanger fouling. The concentration of this heat transfer oil may be from 0 to 30%, optimally at 5% of the total feed to heat exchanger 1. Heat exchanger 1 is preferably operated at about 211° C. to about 255° C. (380°–460° F.), optimally at 250° C. (450° F.), and at about $1.839 \times 10^5$ N/m² (12 psig) to about $2.735 \times 10^5$ N/m² (25 psig) to maximize production of the monomeric products.

Thereafter, the monomeric-containing effluent from heat exchanger 1 is directed to a recovery section. The recovery section comprises a phase separator or recovery drum 3 and distillation tower 5. The monomeric-containing effluent is initially delivered from heat exchanger 1 to phase separator 3 via conduit 15 which permits phase disengagement of any entrained dimers and heat transfer oil from the monomeric products. The entrained dimers and heat transfer oil are taken out as bottoms from phase separator 3 and recycled to heat exchanger 1 via conduits 17 and 19. The monomeric products are taken overhead and passed to distillation tower 5 via conduit 21, wherein a CPD-enriched stream which is essentially free of MCPD and other C6 hydrocarbons is taken out overhead. The MCPD and other C6 hydrocarbons are removed as a sidestream via conduit 23, condensed via heat exchanger 30, passed to dimerizer 8 and placed in a storage tank 25. Any dimeric materials in distillation tower 5 are recovered as tower bottoms and recycled to heat exchanger 1 via conduit 19.

The CPD-enriched stream is discharged overhead from distillation tower 5 via conduit 27. This CPD-enriched stream is condensed via heat exchanger 29 and then passed to dimerizer 7. Dimerizer 7 is operated at about 72° C. to about 94° C. (130°-170° F.), preferably at about 83° C. to about 89° C. (150°-160° F.). Dimerizer 7 is also operated at a pressure in the range between about $4.823 \times 10^4$ N/m$^2$ to about $6.890 \times 10^4$ N/m$^2$ (7-10 psia), preferably at $4.826 \times 10^4$ N/m$^2$ (7 psia) to remove, via vacuum jet (not shown), undimerized acyclic dienes and CPD. In addition, a pumparound loop (not shown) is employed at a rate of about 1 to 15 times the total dimerizer flow rate to remove heat of dimerization, via a heat exchanger (not shown), and to improve dimerization. The dimerization process is operated such that 60 to 85% of the CPD is dimerized; more preferably such that 80% is dimerized. Under these conditions less than 10% of the C$_4$ and/or C$_5$ acyclic dienes will form codimers with CPD. Trimer formation is also minimized in this mode of operation.

The dimerizer effluent is thereafter directed to membrane separator 9 via conduit 31. The dimerizer effluent contacts pervaporation membrane 33 such that a high purity (98-99%) DCPD stream is retained as retentate and wherein any C$_4$ and C$_5$ acyclic dienes and CPD permeate through pervaporation membrane 33 as permeate. The permeate is then discharged from membrane separator 9 via conduit 35 and the high purity DCPD stream is concentrated and discharged via conduit 37.

Figure 2:
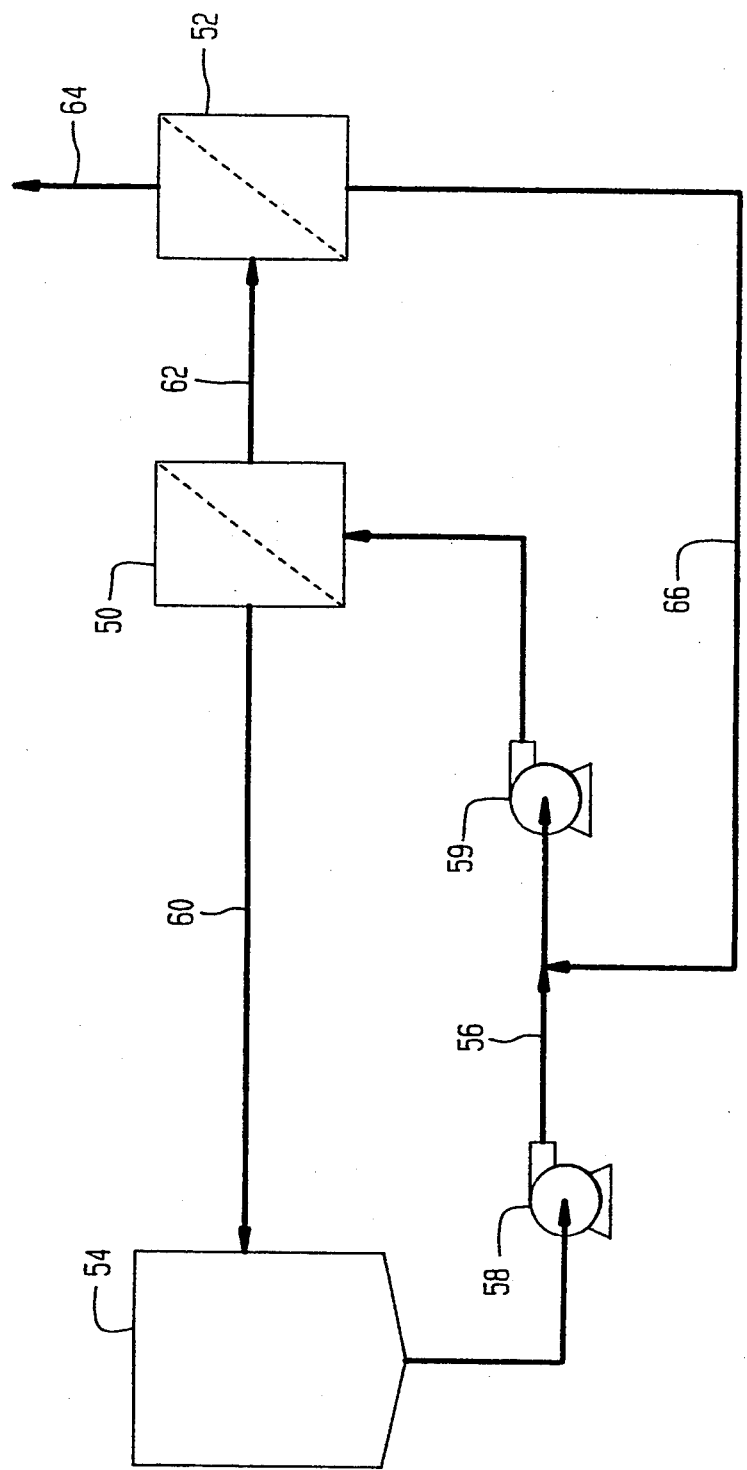
FIG. 2 is a block flow diagram of a series of pervaporation membranes used in the purification of dicyclopentadiene in accordance with another embodiment of the present invention.

FIG. 2 is a schematic representation of another configuration of the membrane separation step wherein two pervaporation membrane units 50 and 52 are connected in series to dimerizer 54. That is, the dimerizer effluent is delivered to first pervaporation membrane unit 50 via conduit 56 and pumps 58 and 59. The dimerizer effluent contacts the pervaporation membrane disposed within membrane unit 50 wherein a DCPD stream is retained as retentate and wherein most C$_4$ and C$_5$ acyclic dienes and CPD pass through the membrane as permeate. The permeate from membrane unit 50 is then recycled to dimerizer 54 via conduit 60. The retentate from membrane unit 50 is then sent on to second membrane unit 52 via conduit 62. The DCPD stream contacts a second pervaporation membrane such that any residual C$_4$ and C$_5$ acyclic dienes and CPD pass through the second pervaporation membrane as permeate and wherein a high purity DCPD stream is retained as retentate. The DCPD stream is then sent via conduit 64 to storage; whereas the permeate is recycled to conduit 56 via conduit 66 for mixing with the dimerizing product which is again passed through first pervaporation membrane unit 50.

EXAMPLE 1

A small, stirred, batch pervaporation cell was used to demonstrate the separation of CPD and acyclics from DCPD. The pervaporation cell had a membrane area of $7.7 \times 10^{-3}$ m$^2$ and an approximate hold up volume of 100 mL. The pervaporation cell was immersed in a temperature controlled water bath to maintain an operating temperature of 70° C. ±2° C. On each of the three membranes tested (i.e., a silicone rubber membrane, a polyester imide membrane and a polyvinyl alcohol membrane), the system was operated in a continuous manner. To ensure that the system did not run dry, the overall permeate flux through the membrane was reduced by lowering the bath temperature to 45° C. during night time operation.

At the beginning of each membrane test, the pervaporation cell was charged with 100 mL of a dimerizer solution comprising dicyclopentadiene (DCPD), cyclopentadiene (CPD), and C$_4$ and C$_5$ acyclics. Bath temperature and vacuum pressure were monitored and recorded hourly during the daytime. The permeate was collected in sample bottles immersed in liquid nitrogen and then stored in liquid nitrogen until shipment for analysis.

The dimerizer solution was sampled several times throughout the test program and used to monitor the concentration of DCPD in the retentate. Samples were allowed to cool to room temperature and then checked for solidification. If solidification occurred, the sample was assumed to be sufficiently enriched in DCPD and the membrane run was stopped after an additional two hours of testing. If solidification did not occur then the run was continued for up to 24 hours. Final retentate samples and initial permeate samples were sent for analysis by gas chromatography (GC) and the results are set forth in Tables 1-3 below.

TABLE 1

(Silicone Rubber Membrane)

| Components | Dimerizer Solution | Retentate | Permeate |
|---|---|---|---|
| C4 Acyclics | 0.104 | 0.000 | 0.268 |
| C5 Acyclics | 1.068 | 0.050 | 2.399 |
| CPD | 0.675 | 0.112 | 1.503 |
| C5 Acyclics | 0.005 | 0.000 | 0.000 |
| C6 Acyclics | 0.020 | 0.000 | 0.031 |
| MCPD | 0.001 | 0.000 | 0.000 |
| C6—C7 Acyclics | 0.000 | 0.000 | 0.000 |
| C7 Acyclics | 0.000 | 0.000 | 0.000 |
| C4-CPD Codimers | 0.165 | 0.107 | 0.204 |
| C5-CPD Codimers | 0.362 | 0.340 | 0.237 |
| DCPD | 96.017 | 97.266 | 94.646 |
| C5-MCPD Codimers | 0.132 | 0.143 | 0.063 |
| CPD-MCPD Codimers | 0.518 | 0.604 | 0.312 |
| MCPD Dimers | 0.001 | 0.001 | 0.000 |
| Oxygenates | 0.000 | 0.000 | 0.000 |
| MCPD-C7 Codimers | 0.019 | 0.015 | 0.217 |
| Trimers | 0.913 | 1.361 | 0.120 |

Notes:
C5 Acyclics prior to CPD include the following isoprene and t-pentadiene-1,3.
C5 Acyclics after CPD include the following c-pentadiene-1,3.

The silicon rubber membrane was formed from a polydimethylsiloxane material.

TABLE 2

(Polyvinyl Alcohol Membrane)

| Components | Dimerizer Solution | Retentate | Permeate |
|---|---|---|---|
| C4 Acyclics | 0.104 | 0.091 | 0.000 |
| C5 Acyclics | 1.068 | 1.017 | 0.000 |
| CPD | 0.675 | 0.656 | 0.065 |
| C5 Acyclics | 0.005 | 0.005 | 0.000 |
| C6 Acyclics | 0.020 | 0.018 | 0.000 |
| MCPD | 0.001 | 0.000 | 0.000 |
| C6—C7 Acyclics | 0.000 | 0.000 | 0.000 |
| C7 Acyclics | 0.000 | 0.000 | 0.000 |
| C4-CPD Codimers | 0.165 | 0.167 | 0.055 |
| C5-CPD Codimers | 0.362 | 0.368 | 0.186 |
| DCPD | 96.017 | 96.065 | 98.440 |
| C5-MCPD Codimers | 0.132 | 0.134 | 0.042 |
| CPD-MCPD Codimers | 0.518 | 0.521 | 0.482 |
| MCPD Dimers | 0.001 | 0.005 | 0.000 |
| Oxygenates | 0.000 | 0.000 | 0.467 |
| MCPD-C7 Codimers | 0.019 | 0.015 | 0.070 |

TABLE 2-continued

(Polyvinyl Alcohol Membrane)

| Components | Dimerizer Solution | Retentate | Permeate |
|---|---|---|---|
| Trimers | 0.913 | 0.936 | 0.192 |

TABLE 3

(Polyester Imide Membrane)

| Components | Dimerizer Solution | Retentate | Permeate |
|---|---|---|---|
| C4 Acyclics | 0.104 | 0.003 | 0.324 |
| C5 Acyclics | 1.069 | 0.223 | 2.959 |
| CPD | 0.675 | 0.171 | 2.047 |
| C5 Acyclics | 0.005 | 0.002 | |
| C6 Acyclics | 0.020 | 0.002 | |
| MCPD | 0.001 | 0.000 | 0.000 |
| C6—C7 Acyclics | 0.000 | 0.000 | 0.000 |
| C7 Acyclics | 0.000 | 0.000 | 0.000 |
| C4-CPD Codimers | 0.165 | 0.144 | 0.185 |
| C5-CPD Codimers | 0.362 | 0.358 | 0.278 |
| DCPD | 96.017 | 97.255 | 93.513 |
| C5-MCPD Codimers | 0.132 | 0.140 | 0.019 |
| CPD-MCPD Codimers | 0.518 | 0.562 | 0.261 |
| MCPD Dimers | 0.001 | 0.000 | 0.054 |
| Oxygenates | 0.000 | 0.000 | 0.000 |
| MCPD-C7 Codimers | 0.019 | 0.021 | 0.164 |
| Trimers | 0.913 | 1.119 | 0.121 |

Of the three membranes tested, the polydimethylsiloxane and polyester imide membranes showed positive results during testing. The final retentate samples from those membranes solidified at room temperature indicated that a majority of the initial 0.675 wt. % CPD was removed. Analysis of the retentate samples showed a final CPD level of 0.112 wt. % after 18 hours of testing with the polydimethylsiloxane membrane and 0.171 wt. % CPD after 24 hours of testing with the polyester imide membrane.

Both the polydimethylsiloxane membrane and the polyester imide membrane exhibited similar overall results. Table 4 below summarizes the pervaporation results and includes flux and mass transfer coefficients.

TABLE 4

(Comparison of Permeate Fluxes After One Hour)

| Membrane | Permeate Sample Volume (mL) | CPD Conc. in Permeate (wt. %) | CPD Flux (gmh) | Total Flux (gmh) | Permeation MTC ($\mu$m/s) | Deplet. MTC* ($\mu$m/s) |
|---|---|---|---|---|---|---|
| Silicone Rubber | 4.7485 | 1.503 | 9.076 | 604 | 0.402 | 0.224 |
| PVA | 2.4990 | 0.065 | 0.110 | 169 | 0.005 | 0.004 |
| Polyester Imide | 5.7267 | 2.047 | 10.893 | 532 | 0.482 | 0.137 |

Notes:
gmh denotes grams/(square meter-hour).
*Depletion MTC based on one day of separation by pervaporation.

The permeation MTC (or k, with units of m/s) is calculated by the following equation:

$$k = J/C$$

which defines the target component permeation rate. J (expressed as kg/m$^2$s) is the target component flux and C (expressed at kg/m$^3$) is the concentration of the target component in the feed. The MTC allows flux data to be compared, independently of feed concentration and also indicates if there is any membrane swelling due to liquid absorption by the membrane. If there is no membrane swelling, the MTC should be constant for any given temperature.

The depletion MTC is defined by $$k = (Q/A)ln\{X_{in}/X_{out}\}$$

wherein A is the system membrane area (m$^2$), C is the concentration of the target component in the bulk liquid (kg/m$^3$), k is the MTC of the target component, J is the target component flux (measured as the wt. % of target component in the total flux) (kg/m$^2$s), Q is the volumetric flow rate through the system (m$^3$/s), $X_{in}$ is the target component concentration entering the pervaporation system (weight fraction), and $X_{out}$ is the target component concentration leaving the pervaporation system (weight fraction).

The depletion MTC is a measure of the rate of decrease of the target component from the bulk liquid. Since the target component can only leave by permeating through the membrane, the depletion MTC should equal the permeate MTC.

The separation factor, $\alpha$, is a measure of the effectiveness of separation and is estimated by the following equation:

$$\alpha = \frac{(Y_i/Y_j)}{(X_i/X_j)}$$

where Y is the concentration of either component (i) or (j) in the permeate and X is the concentration of either component (i) or (j) in the liquid feed. Since $\alpha$ is dimensionless, X and Y may be any convenient but consistent concentration unit. Weight fractions are, however, used for X and Y for consistency with equations used later in this report. Although the separation factor is a convenient way of communicating effectiveness of separation, it provides no useful information required to design a pervaporation system.

The CPD permeation mass transfer coefficient (MTC) and CPD depletion MTC show a more dramatic change for the polyester imide membrane than for the polydimethylsiloxane membrane as a function of operating temperature. The depletion MTC, however, accounts for the segment of testing carried out at the reduced operating temperature. Typically, a reduction in the operating temperature by 25° C., reduces membrane permeability by 3 to 5 times. The MTC's for the polyester imide membrane are in-line with these expectations indicating that the polyester imide membrane test data is in agreement with predicted membrane characteristics. The reduction in the MTC is not as dramatic for the polydimethylsiloxane membrane and may indicate the performance may be affected by another mechanism such as the hydrodynamics of the test cell.

The polyester imide membrane demonstrated somewhat better selectivity for the CPD compared to the polydimethylsiloxane membrane. The permeate was enriched by almost two and a half times for the polydimethylsiloxane membrane, whereas the polyester imide membrane demonstrated enrichment of three times.

Due to the high temperatures and pressures used during these tests, all of the membranes exhibited a significant amount of DCPD permeation. DCPD permeation is undesirable and can be controlled by monitoring the temperature and pressure of the pervaporation membrane separator.

The final retentate solution from the polyvinyl alcohol run did not solidify at room temperature. This indicated that a majority of the CPD had not been removed from the DCPD feed solution. GC analysis showed the CPD concentration was only marginally reduced from 0.675 wt. % to 0.656 wt. % over a 28 hour period.

After testing, all three membranes were examined for signs of decomposition, blistering or degradation. After at least 18 hours of testing, none of the three membranes showed any major signs of degradation. The polydimethylsiloxane and polyester imide membranes appeared unaffected by the DCPD solution. The polyvinyl alcohol membrane appeared to have several tiny black spots on the membrane surface. These spots could indicate the beginning of membrane blistering.

from DCPD solution using a polydimethylsiloxane membrane.

A small, stirred, batch pervaporation cell was used to conduct a total of five runs. The runs were conducted at either a temperature of 50° C. or 70° C. and at pressures of either 75 torr or 150 torr. Testing at 300 torr as originally planned was not possible due to the significant swelling of the membrane at the rougher vacuum pressures and the very low flux rates which required significant run time to collect minimum permeate volumes.

The operational procedures followed were similar to Example 1 above, except that the vacuum pressure of the system was controlled by a vacuum control valve. Permeate samples were collected in bottles immersed in liquid nitrogen and then diluted 10:1 with toluene. The samples were then analyzed by gas chromatography.

Tables 5, 6, and 7 below set forth the results of this pervaporation study using a polydimethylsiloxane membrane wherein the results from Table 1, Example 1, have also been included for comparison at 70° C. and high vacuum (i.e., run #1 in each table is for comparison purposes only). Fluxes, mass transfer coefficients (MTC) and separation factors have been calculated based on CPD and the two major acyclics, $C_4$ acyclics and $C_5$ acyclics.

TABLE 5

(Separation of DCPD from CPD)

| Run | Liquid Temp. (°C.) | Vacuum Pressure (torr) | CPD Conc. in Feed | CPD Conc. in Ret. | CPD Conc. in Per. | CPD Flux (g/m2h) | Permeation MTC (μm/s) | Sep. Factor |
|---|---|---|---|---|---|---|---|---|
| 1 | 70 | 25 | 0.675% | 0.634% | 1.503% | 8.4 | 0.37 | 2 |
| 2 | 71 | 72.5 | 0.675% | 0.410% | 13.66% | 15.2 | 0.67 | 23 |
| 3 | 71 | 147.5 | 0.410% | 0.325% | 7.497% | 7.5 | 0.45 | 20 |
| 4 | 70 | 70 | 0.325% | 0.305% | 4.045% | 7.5 | 0.69 | 13 |
| 5 | 52 | 70 | 0.634% | 0.523% | 25.75% | 3.4 | 0.16 | 54 |
| 6 | 53 | 142.5 | 0.628% | 0.572% | 23.30% | 0.8 | 0.04 | 48 |

TABLE 6

(Separation of DCPD from C4 Acyclics)

| Run | Liquid Temp. (°C.) | Vacuum Pressure (torr) | C4 Conc. in Feed | C4 Conc. in Ret. | C4 Conc. in Per. | C4 Flux (g/m2h) | Permeation MTC (μm/s) | Sep. Factor |
|---|---|---|---|---|---|---|---|---|
| 1 | 70 | 25 | 0.104% | 0.000% | 0.268% | 1.5 | 0.43 | 3 |
| 2 | 71 | 72.5 | 0.104% | 0.037% | 3.096% | 3.4 | 0.99 | 31 |
| 3 | 71 | 147.5 | 0.037% | 0.021% | 1.426% | 1.2 | 0.95 | 39 |
| 4 | 70 | 70 | 0.021% | 0.014% | 0.559% | 1.0 | 1.47 | 27 |
| 5 | 52 | 70 | 0.094% | 0.046% | 8.684% | 1.2 | 0.37 | 101 |
| 6 | 53 | 142.5 | 0.084% | 0.054% | 12.67% | 0.4 | 0.15 | 173 |

TABLE 7

(Separation of DCPD from C5 Acyclics)

| Run | Liquid Temp. (°C.) | Vacuum Pressure (torr) | C5 Conc. in Feed | C5 Conc. in Ret. | C5 Conc. in Per. | C5 Flux (g/m2h) | Permeation MTC (μm/s) | Sep. Factor |
|---|---|---|---|---|---|---|---|---|
| 1 | 70 | 25 | 1.068% | 0.050% | 0.224% | 1.3 | 0.04 | 0.21 |
| 2 | 71 | 72.5 | 1.068% | 0.621% | 24.49% | 27.3 | 0.76 | 30 |
| 3 | 71 | 147.5 | 0.621% | 0.500% | 13.84% | 11.4 | 0.55 | 26 |
| 4 | 70 | 70 | 0.500% | 0.438% | 7.230% | 13.4 | 0.80 | 16 |
| 5 | 52 | 70 | 0.997% | 0.786% | 54.18% | 7.3 | 0.22 | 117 |
| 6 | 53 | 142.5 | 0.993% | 0.866% | 55.11% | 1.9 | 0.06 | 122 |

EXAMPLE 3

This experiment was undertaken to investigate the performance enhancement which may be achieved by operating the pervaporation system at rough vacuum (i.e., greater than 25 torr). The objectives of this experiment were to determine the effect of vacuum pressure on the efficiency of separation of CPD and acyclics As noted in comparison run #1 of Table 5, the separation factor of CPD and acyclics from the DCPD at 70° C. and 25 torr was only 3. This resulted in the passage of high concentrations of DCPD into the permeate.

For run #2 in Tables 4, 5, and 6 above, the pervaporation system was operated at a pressure of 150 torr (±10 torr). At this rougher vacuum, the separation factor of CPD and acyclics from the DCPD solution increased to 20. When the temperature was dropped to 50° C. the separation factor increased to 50. This indicates that operating at rough vacuum and lower temperature will significantly reduce the amount of DCPD permeated through the membrane and will eliminate the need for reprocessing the permeate to salvage the DCPD.

At a vacuum pressure of 150 torr and 70° C. the removal rate or flux of CPD from the DCPD solution (with approximately 4 wt. % CPD) was 6.2 g/m$^2$h. At 25 torr and 70° C., the flux of CPD was 8.4 g/m$^2$h, indicating that rougher vacuum pressures did not significantly affect the removal rate of the CPD from the solution, whereas at the lower temperature of 50° C. the removal rate of CPD declined 75% to 0.8 g/m$^2$h.

The results from this Example 2 indicate that rough vacuum operation and lower temperatures show significant separation enhancement. However, the results also indicate that lower temperatures cause the flux of CPD and acyclics to dramatically decline.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A process for purifying crude dicyclopentadiene which comprises the steps of:
   a. cracking said crude dicyclopentadiene to form a monomeric-containing effluent which comprises cyclopentadiene and at least one monomer selected from the group consisting of: C$_4$ acyclic dienes, C$_5$ acyclic dienes, and methylcyclopentadiene;
   b. separating said monomeric-containing effluent into a cyclopentadiene-enriched stream and a cyclopentadiene-poor stream;
   c. dimerizing said cyclopentadiene-enriched stream to form a dimerizer effluent;
   d. contacting a membrane separator under pervaporation conditions with said dimerizer effluent wherein said C$_4$ acyclic dienes, said C$_5$ acyclic dienes and said cyclopentadiene permeate through said membrane separator and wherein a dicyclopentadiene product having a purity of at least about 98% is retained as retentate.

2. The process according to claim 1 further comprising a step of condensing said cyclopentadiene-enriched stream of step (b) prior to the dimerizer step (c).

3. The process according to claim 1 wherein said membrane separator comprises a pervaporation membrane.

4. The process according to claim 4 wherein said pervaporation membrane is selected from the group consisting of: any rubbery membrane, polyester imide membranes, and polyurea/urethane membranes.

5. The process according to claim 1 wherein the cracking of said crude dicyclopentadiene in step (a) is conducted in a shell and tube heat exchanger.

6. The process according to claim 1 wherein the separating of said monomer effluent into a cyclopentadiene-enriched stream and a cyclopentadiene-poor stream is conducted in a distillation tower.

7. The process according to claim 5 wherein an inert hydrocarbon heat transfer oil having a boiling point greater than said crude dicyclopentadiene is added to said heat exchanger in amount between about 0 to about 30%, based on the total feed to said heat exchanger, prior to cracking of said crude dicyclopentadiene and wherein said monomeric-containing effluent also includes said heat transfer oil.

8. The process according to claim 5 wherein said heat exchanger is operated at a temperature in the range between about 211° C. to about 255° C.

9. The process according to claim 5 wherein said heat exchanger is operated at a pressure in the range between about $1.839 \times 10^5$ N/m$^2$ to about $2.735 \times 10^5$ N/m$^2$.

10. The process according to claim 7 further comprising a step of recovering said monomeric-containing effluent of step (a) prior to separating step (b).

11. The process according to claim 10 wherein the recovery of said monomeric-containing effluent is conducted in a phase separator.

12. The process according to claim 11 wherein said monomeric-containing effluent is separated via said phase separator into monomeric products which are sent to separating step (b) and entrained dimers and heat transfer oil which are taken out as bottoms from said phase separator.

13. The process according to claim 12 wherein said entrained dimers and heat transfer oil are recycled to said heat exchanger.

14. The process according to claim 1 wherein said dimerizing step (c) is operated at a temperature in the range between about 72° C. to about 94° C.

15. The process according to claim 1 wherein said dimerizing step (c) is operated at a pressure in the range between about $4.823 \times 10^4$ N/m$^2$ to about $6.890 \times 10^4$ N/m$^2$.

16. The process according to claim 1 wherein said dimerizing step (c) is operated such that about 60 to about 85% of said cyclopentadiene is dimerized; whereby less than 10% of the C$_4$ and/or C$_5$ acyclic dienes will form codimers with said cyclopentadiene and whereby trimer formation is also minimized.

17. The process according to claim 1 wherein said membrane separator comprises two pervaporation membranes connected in series.

* * * * *